United States Patent
Fan et al.

(10) Patent No.: US 8,338,627 B2
(45) Date of Patent: Dec. 25, 2012

(54) PROCESS FOR PRODUCING EPOXIDES

(75) Inventors: William W. Fan, Lake Jackson, TX (US); Christian D. Kneupper, Brazoria, TX (US); Sascha Noormann, Gruenendeich (DE); Ranate Patrascu, Stade (DE); Bruce D. Hook, Lake Jackson, TX (US); Charles W. Lipp, Lake Jackson, TX (US); Michael D. Cloeter, Lake Jackson, TX (US); Heinz Groenewald, Hammah (DE)

(73) Assignee: Dow Global Technologies LLC, Midland, MI (US)

( * ) Notice: Subject to any disclaimer, the term of this patent is extended or adjusted under 35 U.S.C. 154(b) by 551 days.

(21) Appl. No.: 12/512,227

(22) Filed: Jul. 30, 2009

(65) Prior Publication Data

US 2010/0029960 A1 Feb. 4, 2010

Related U.S. Application Data

(60) Provisional application No. 61/085,734, filed on Aug. 1, 2008.

(51) Int. Cl.
*C07D 301/24* (2006.01)
(52) U.S. Cl. .......................... 549/520; 549/522
(58) Field of Classification Search .................. 549/520, 549/521, 522
See application file for complete search history.

(56) References Cited

U.S. PATENT DOCUMENTS

| | | | | |
|---|---|---|---|---|
| 2,177,419 | A | * | 10/1939 | Engs et al. ................ 549/521 |
| 3,886,187 | A | | 5/1975 | Bartholome et al. |
| 4,113,746 | A | | 9/1978 | Kawabe et al. |
| 4,496,753 | A | | 1/1985 | Kwon et al. |
| 4,634,784 | A | | 1/1987 | Nagato et al. |
| 5,486,627 | A | * | 1/1996 | Quarderer et al. ......... 549/521 |
| 5,532,389 | A | | 7/1996 | Trent et al. |
| 2008/0015370 | A1 | | 1/2008 | Hook et al. |

FOREIGN PATENT DOCUMENTS

| | | |
|---|---|---|
| EP | 0421379 | 4/1991 |
| EP | 1059278 | 12/2000 |
| GB | 2173496 | 10/1986 |
| GB | 2173496 A | 10/1986 |
| JP | 1994-025196 B2 | 10/1991 |
| JP | 06-025196 A | 2/1994 |
| JP | 6025196 | 3/1995 |
| RU | 2198882 | 2/2003 |
| RU | 2198882 C1 | 2/2003 |
| WO | 2006/020234 | 2/2006 |
| WO | 2006/020234 A1 | 2/2006 |

OTHER PUBLICATIONS

Mahajan, A.L.J., Kirwan, D.J., Micromixing Effects in a Two-Impinging-Jets Precipitator, AIChE J. 1996, vol. 42, pp. 1801-1814.
Johnson, B.K., Prud'Homme, R.KL, Chemical processing and Micromixing of Confined Impinging Jets, AIChe J. 2003, vol. 49, pp. 2264-2282.
Demyanovich, R.J., Bourne, J.R., Rapid Micromixing by the Impingement of Thin Liquid Sheets. 1. A Photographic Study of the Flow Patter, Ind. Eng. Chem. Res., 1989, pp. 825-830.
Davies, J.T., A Physical Interpretation of Drop Sizes in Homogenizers and Agitated Tanks, Including the Dispersion of Viscous Oils, Chemical Engineering Science, 1987, vol. 42, pp. 1671-1676.
Fan, William W. et al, Process for Producing Epoxides, U.S. Appl. No. 12/508,435, filed Jul. 23, 2009.
Fan, William W. et al, Process for Producing Epoxides, U.S. Appl. No. 12/508,465, filed Jul. 23, 2009.
Maki, K. et al, Epichlorohydrin Preparation—From 2, 3-di:chloro-1-propanol and/or 1, 3-di:chloro-1-propanol by Treatment with Alkali, Japanse Patent No. JP 04060111 (JP60258172), Dec. 20, 1985 (English Abstract).
English Patent Abstract of GB 2173496 from esp@cenet, published Oct. 15, 1986, 1 page.
English Patent Abstract of JP 06-025196 from Patent Abstracts of Japan, published Jan. 2, 1994, 2 pages.

* cited by examiner

*Primary Examiner* — Taylor Victor Oh

(57) ABSTRACT

A process for producing epoxide, the process including contacting an organic phase including at least one halohydrin(s) with at least one aqueous phase including a base in a plug-flow mixer/reactor system to disperse the organic phase in the aqueous phase via a mixing device imparting a power-to-mass ratio of at least 0.2 W/kg to convert at least a portion of the at least one halohydrin to an epoxide.

15 Claims, No Drawings

PROCESS FOR PRODUCING EPOXIDES

CROSS-REFERENCE TO RELATED APPLICATION

This application, pursuant to 35 U.S.C. §119(e), claims priority to U.S. Provisional Application Ser. No. 61/085,734, filed Aug. 1, 2008, which is hereby incorporated by reference in its entirety.

FIELD OF THE DISCLOSURE

Embodiments disclosed herein relate generally to processes and apparatus to produce epoxides, particularly to processes and apparatus for forming epoxides via the corresponding halohydrins. More specifically, embodiments disclosed herein relate to dehydrohalogenation processes and apparatus for the continuous production of epoxides by the reaction of halohydrins with alkali.

BACKGROUND

Epoxides, including propylene oxide, butylene oxide, epichlorohydrin, and the like, are widely used precursors for the production of other compounds. Most epoxides are formed via halohydrin intermediates, and these processes are well known to those skilled in the art, such as disclosed in U.S. Pat. No. 5,532,389 and British Patent No. 2,173,496. The halohydrins are most often reacted with an aqueous alkali stream to produce epoxides and the subsequent halide salt. The epoxide-water azeotrope is advantageously stripped from the aqueous stream to minimize by-product losses resulting from the reaction of water with epoxide to form glycols, such as ethylene glycol, propylene glycol, 3-chloro-1,2-propandiol, glycidol, and glycerine. This overhead product, including water and epoxide, is then condensed and separated in a liquid-liquid phase separator to form an aqueous fraction and an organic fraction containing the crude epoxide, which may be further purified. The aqueous fraction from the overhead is returned to the distillation column as reflux. The hydrolysis of the epoxide can be further enhanced by the presence of either acid or base, and is reduced at a pH of 7. The process of ring closure by the action of an alkali is also described by the terms epoxidation, saponification, and in the case of the halogen chlorine, dehydrochlorination.

In industrial processes, halohydrins are made by reacting low molecular weight olefin-containing compounds, such as propylene, butylene, and allyl chloride, with chlorine (or other halogens) and water in a reaction referred to as hypochlorination. Thus propylene and butylene are converted to chlorohydrins and allyl chloride to dichlorohydrins, and subsequently to their respective epoxides (e.g., propylene oxide, butylene oxide, and epichlorohydrin). This process produces both isomers of the halohydrins, and the resulting halohydrins are often dilute in water (<10% by weight) and contain an equivalent of haloacid from the reaction. The halohydrin stream produced by hypohalogenation may then be fed directly to a reactive distillation column with an alkali, or first, to a pre-reactor for neutralization of the haloacid and partial conversion of the halohydrin before introduction into the reactive distillation column. For example, Japanese Patent No. JP 1994-025196(B2) discloses a process where dilute dichlorohydrins are mixed with $Ca(OH)_2$ at 40° C. in a pre-reactor and then fed to a reactive distillation column where the epoxide (epichlorohydrin) is stripped overhead with water and phase separated from the water in the overhead phase separator to obtain epichlorohydrin.

Another technology, used to a lesser extent in industry, is the reaction of glycols with HCl and a carboxylic acid catalysis to produce the halohydrin, such as disclosed in U.S. Patent Application Publication No. 20080015370. As described therein, mostly one isomer of the halohydrin (1,3-dichlorohydrin) is produced, and the remainder of the stream contains less than 30% water and less than 10% HCl, each by weight. This halohydrin stream is fed with a 10% NaOH stream to a reactive distillation column where epichlorohydrin is stripped overhead with water and phase separated from the water in the overhead phase separator to obtain epichlorohydrin.

A third technology, used specifically for the production of epichlorohydrin, is the catalytic acetoxylation of propylene into allyl acetate, hydrolysis of the allyl acetate into allyl alcohol, and catalytic chlorination of the allyl alcohol into dichlorohydrin, as disclosed in U.S. Pat. No. 4,634,784. As disclosed therein, mostly one isomer of the halohydrin (2,3-dichlorohydrin) is produced, and the remainder of the stream contains less than 20% water and 5% HCl, each by weight. This halohydrin stream is fed with a 9.5% $Ca(OH)_2$ slurry to a column where epichlorohydrin is stripped overhead with water and phase separated from the water in the overhead phase separator to obtain epichlorohydrin.

Three main reactions occur during the process to convert halohydrins to epoxides: neutralization of the haloacid, dehydrohalogenation of the halohydrin, and the hydrolysis of the epoxide to glycol. The dehydrohalogenation of the halohydrin, for example, may be performed with an alkali. The halohydrin can be dilute in aqueous or mostly organic stream, and often consists of two isomers as well as haloacid. The base is typically an aqueous stream or slurry consisting of NaOH or $Ca(OH)_2$, with or without the presence of a salt, such as NaCl and $CaCl_2$. In order to avoid yield losses of the epoxide to hydrolysis, the epoxide is often stripped during the reaction in a distillation column and pH is maintained as close to neutral as possible, as the hydrolysis rate is catalyzed by both acid and base. The glycols produced, and some residual organics, are not strippable and are lost in the aqueous stream with the salt formed, which exits the bottom of the distillation column and constitute the major yield loss from the dehydrohalogenation process. The bottom aqueous stream may be treated before discharge or recycle. Thus, hydrolysis losses not only impact epoxide yield, but also wastewater treatment cost and capital investment.

A wide variety of embodiments of processes and apparatus for the dehydrohalogenation of mostly organic halohydrins have been proposed in the prior art. For example, Russian Patent No. 2,198,882 disclose mixing an anhydrous dichlorohydrin stream, distilled from the dilute stream containing a mixture of dichlorohydrin isomers from hypochlorination of allyl chloride with chlorine and water, with 28% NaOH in a continuous stirred tank reactor (CSTR) to produce epichlorohydrin, which is then subsequently stripped. This system is biphasic, with an organic dichlorohydrin phase and an aqueous phase with the NaOH. As all reactions occur primarily in the aqueous phase, mass transfer is a major factor to obtaining high epoxide yields. U.S. Pat. No. 4,496,753 discloses a similar biphasic system, with the dichlorohydrins in an organic solvent ($CCl_4$) in a 2-stage reactor with a CSTR followed by a plug flow reactor (PFR). However, these methods have technical and economical drawbacks. One such drawback is the need for additional equipment, such as a CSTR, and another drawback is that backmixing in the CSTR exposes epoxide to hydrolysis with the incoming acid and base, depending on the intensity of mixing. In the case with a solvent, an addition distillation column for solvent recovery is needed, and depending on the partitioning of the epoxide between the two phases, may also lead to additional epoxide losses.

U.S. Pat. No. 4,634,784 (the '784 patent) discloses catalytic acetoxylation of propylene into allyl acetate, hydrolysis of the allyl acetate into allyl alcohol, catalytic chlorination of the allyl alcohol into dichlorohydrin, and the dehydrochlorination of the dichlorohydrin into epichlorohydrin. Predominately only the 2,3-dichlorohydrin isomer is produced in a 75% by weight organic stream. This system is biphasic, with an organic dichlorohydrin phase and an aqueous phase or slurry with the base. As all reactions occur primarily in the aqueous phase, mass transfer is a major factor to obtaining high epoxide yields. Several methods of dehydrochlorination are described: the dichlorohydrin and milk of lime is (1) fed directly to the top of a distillation column, (2) mixed while stirring, and (3) reacted in an inert solvent insoluble to water. The disadvantages of methods (2) and (3) have already been discussed above. For method (1), the direct feeding to a distillation column, the mixing intensity is not as great on the plates in the distillation column as in the cases with CSTR, resulting in lower conversions. The example given in the '784 patent shows a 2,3-dichlorohydrin stream fed with a 9.5% $Ca(OH)_2$ slurry to a column to obtain a conversion of 88% and a selectivity of 97%. The low dichlorohydrin conversion dictates larger recovery equipment, higher recycle, and higher cost.

WO 2006/020234 discloses the reaction of glycols with HCl and carboxylic acid catalysis to produce the halohydrin, particularly for glycerine to dichlorohydrins to epichlorohydrin. The dichlorohydrin produced is predominately the 1,3-dichlorohydrin isomer, which has a much faster dehydrochlorination reaction rate than the 2,3-dicholohydrin isomer. The base used can be NaOH or $Ca(OH)_2$ and is preferably 20-60% by weight. This system is biphasic, with an organic dichlorohydrin phase and an aqueous phase with the base. As all reactions occur primarily in the aqueous phase, mass transfer is a major factor to obtaining high epoxide yields. No mention is made of importance of mixing intensity and high specific interfacial surface area as the reaction is mass transfer limited. WO 2006/020234 gave an example of feeding the dichlorohydrin with 10% NaOH to a distillation column and obtained good product quality with no mention of yield.

Accordingly, there exists a need for improved processes and apparatus for the dehydrohalogenation of halohydrins in which the overall by-product hydrolysis reaction may be reduced in order to obtain good epoxide selectivity and conversion.

SUMMARY OF THE DISCLOSURE

In one aspect, embodiments disclosed herein relate to a process for producing epoxides, the process including contacting an organic phase including at least one halohydrin(s) with at least one aqueous phase including at least one base in a plug-flow mixer/reactor system to disperse the organic phase in the aqueous phase via a mixing device imparting a power-to-mass ratio of at least 0.2 W/kg to convert at least a portion of the at least one halohydrin to an epoxide. Surprisingly, both reaction rates and product yields can be improved when sufficient power is added during mixing to generate a high surface area.

In another aspect, embodiments disclosed herein relate to a process for producing epichlorohydrin, the process including contacting an organic phase including at least one dichlorohydrin with at least one aqueous phase including at least one base in a plug-flow mixer/reactor system to disperse the organic phase in the aqueous phase via a mixing device imparting a power-to-mass ratio of at least 0.2 W/kg to convert at least a portion of the at least one dichlorohydrin to epichlorohydrin.

Other aspects and advantages will be apparent from the following description and the appended claims.

DETAILED DESCRIPTION

In one aspect, embodiments disclosed herein relate generally to processes and apparatus to produce epoxides, particularly to processes and apparatus for forming epoxides via halohydrins. In a more specific aspect, embodiments disclosed herein relate to dehydrohalogenation processes and apparatus for the continuous production of epoxides by the reaction of the halohydrins with alkali, where the epoxide may be distilled from the alkali reaction mixture.

As used herein, the term "epoxide" refers to a compound containing oxygen attached to separate saturated adjacent carbon atoms. Epoxides, also known as oxiranes, are cyclic ethers and may contain from 2 to about 10 carbon atoms that are arranged as linear, branched, or cyclic, that are attached by a carbon bond to the epoxide group. The carbons attached to the epoxide may be unsubstituted, but may also be inertly substituted. By "inertly substituted" it is meant that the epoxide is substituted with any group which does not undesirably interfere with formation of the halohydrin or the epoxide. Inert substituents include chlorine, bromine, fluorine, phenyl, and the like. Examples of epoxides may include ethylene oxide, propylene oxide, epichlorohydrin, and butylene oxide, among others.

As used herein, the term "halohydrin" refers to a compound containing at least one hydroxyl group and at least one halogen atom attached to separate saturated carbon atoms, such as adjacent carbon atoms. Halohydrins may contain from 2 to about 10 carbon atoms and may be linear, branched, or cyclic. Halohydrins may be unsubstituted, but may also be inertly substituted. By "inertly substituted" it is meant that the halohydrin is substituted with any group which does not undesirably interfere with formation of the halohydrin or the epoxide. Inert substituents include chlorine, bromine, fluorine, phenyl, and the like. Examples of halohydrins may include bromohydrins and chlorohydrins, such as, but not limited to, 1-chloro-2-ethanol; 1-chloro-2-propanol; 2-chloro-1-propanol; 1,3-dichloro-2-propanol; 2,3-dichloro-1-propanol; 1-chloro-2-butanol; and 2-chloro-1-butanol.

As used herein, the terms "by-product" and "hydrolysis product" refer to a compound produced by the hydrolysis of the epoxide, including derivative compounds from the hydrolyzed compounds. Examples include ethylene glycol, propylene glycol, 3-chloro-1,2-propandiol, glycidol, glycerine, butylenes glycol, and their corresponding ethers.

Epoxides may be produced in good yields according to embodiments disclosed herein by the dehydrohalogenation of halohydrin with a base. A mostly organic stream, including a halohydrin and optionally haloacid, may be contacted with an aqueous stream including a base. To minimize acid or base catalyzed hydrolysis of the epoxide, high mixing intensity may be used to advantageously utilize the difference in reaction rates of the neutralization, dehydrohalogenation, and hydrolysis reactions. High mixing intensity may provide for better pH control when contacting halohydrin streams with acid and base streams, such as disclosed in U.S. Pat. No. 3,886,187, where turbulent jet mixing was employed for contact of two aqueous streams for pH control. The contacting of the components may be facilitated by passing the mixture through a mixer/reactor according to embodiments disclosed herein above a critical power-to-mass ratio of at least 0.2 watts per kilogram (W/kg). In other embodiments, the phases are dispersed using a power-to-mass ratio of at least 3 W/kg.

A power per mass ratio is calculated from the sum of the kinetic energy of the inlet streams together with the mass in the mixing zone:

$$\text{Power} = \frac{1}{2} * (m_1 v_1^2 + m_2 v_2^2)$$

$$\text{Mass} = \text{density} * \text{mixing volume},$$

where $m_1$ and $v_1$ are the mass rate and velocity, respectively, for stream 1 and $m_2$ and $v_2$ are the mass rate and velocity, respectively, for stream 2. For correlation purposes, the mixing volume for the impingement mixer is taken as the volume of a cylinder defined by a diameter of the mixing chamber, D with an axial length of 2D. The mixing volume of a static mixer is defined by the volume of a cylinder of the same diameter and length. The power per mass ratio is defined accordingly. It is noted that the Power defined by the above equation is strictly true only for inelastic collisions of the jets; however, for purposes of correlation it has been found suitable for use herein, recognizing that a portion of the kinetic energy is lost to deflection and acceleration of the combined fluids rather than mechanical energy of mixing. See, for example, Mahajan, A. J., Kirwan, D. J., "Micromixing Effects in a Two-Impinging-Jets Precipitator," *AIChE J.* 1996, 42, 1801-1814, Johnson, B. K., Prud'homme, R. K., "Chemical Processing and Micromixing of Confined Impinging Jets," AIChE J., 2003, 49, 2264-2282, and Demyanovich, R. J., Bourne, J. R., "Rapid Micromixing by the Impingement of Thin Liquid Sheets. 1. A Photographic Study of the Flow Pattern," *Ind. Eng. Chem. Res.,* 1989, 28, 825-830.

For mass transfer calculations, it is desirable to correlate the power per mass to a relevant droplet diameter so that interfacial area can be inferred. The maximum stable drop size, $d_{max}$, represents the diameter where a balance exists between the turbulent shearing forces that tear a droplet apart and the restoring force of interfacial tension. It is commonly correlated with power per mass ratio, $P_M$, with an equation of the form:

$$d_{max} = \text{constant} * (\sigma/\rho_c)^{0.6} P_M^{-0.4}$$

where $\sigma$ is the interfacial tension and $\rho_c$ is the density of the continuous phase. The constant in the equation is commonly between 0.5 and 1. The Sauter mean diameter, $d_{32}$, is then commonly taken as related to $d_{max}$ by a proportionality factor of 1.5;

$$d_{max} = 1.5\ d_{32}$$

The $d_{32}$ (also referred to as the volume-to-surface area diameter) is particularly useful for interfacial processes such as mass transfer calculations because it represents the diameter of a sphere that has the same volume to surface area ratio as the full droplet size distribution. For more discussion on these topics, see for example, Davies, J. T., "A Physical Interpretation of Drop Sizes in Homogenizers and Agitated Tanks, Including the Dispersion of Viscous Oils," *Chem. Eng. Sci.,* 1987, 42, 1671-1676.

In some embodiments the mixer/reactor may include a pipe mixer/reactor having internal mixing elements designed to provide adequate local power to mass ratio (energy dissipation) to break up and disperse the organic phase in order to provide sufficient interfacial area to ensure full reaction within 10 seconds. Typically, this requires droplets with a $d_{32}$ of less than 1000 microns. The mixing elements may be located within the reactor at a point of impingement of the organic and aqueous flow into the pipe, may be located elsewhere along the length of the pipe, or a combination thereof. In some embodiments, the initial contacting may be provided by an impingement mixer, jet(s)-in-cross-flow (tee-mixers, spargers, etc.), an inline dynamic mixer, a rotorstator mixer, or combinations thereof.

In another embodiment, it has been found that use of a static mixer presents an advantage of providing residence time in a region of high uniform power-to-mass ratio, maintaining high interfacial area by providing further droplet break-up and minimizing the impact of surface area reduction from droplet coalescence.

In another embodiment, it has been found that epoxide product, due to its low solubility in the aqueous phase where it forms, nucleates and forms a third liquid phase. This is an advantageous mode of operation as the epoxide is substantially removed from the phases containing haloacid, base, and water that are required for undesired hydrolysis reactions. As the original halohydrin organic phase is reacted away, the mixture returns to a biphasic mode with an aqueous phase and an epoxide-dominated organic phase. A solvent added to the reaction mixture that can limit the epoxide solubility in the basic aqueous phase would also be beneficial in minimizing undesired hydrolysis reactions.

In another embodiment, it has been found that, for a biphasic medium with the halohydrin and base, mixing is needed not only for pH control but to control the mass transfer rate of the halohydrin from the organic phase to the aqueous base. The mixer/reactor system described above, providing a shear level to disperse the two phases, may improve mass transfer between the two phases, thus obtaining a high conversion and selectivity. It is another advantage of embodiments disclosed herein that the same equipment and process may be used for single and biphasic systems.

In some embodiments, the halohydrin feed stream may include predominately one isomer of the halohydrin. For example, in certain embodiments, the halohydrin feed may include from 25 to 100 percent of the halohydrin isomers, a haloacid such as hydrochloric acid (HCl) in an amount ranging from 0 to about 20 weight percent, and up to about 75 weight percent water. In other embodiments, the halohydrin feed may include from 55 to 100 percent of the halohydrin isomers, a haloacid such as hydrochloric acid (HCl) in an amount ranging from 0 to about 10 weight percent, and up to about 30 weight percent water. The total halohydrin feed may be organic and single phase, or may be biphasic.

The base may include an aqueous alkali metal hydroxide, such as sodium hydroxide, potassium hydroxide, calcium hydroxide, or mixtures thereof. In some embodiments, the aqueous phase may also include an alkali metal salt, such as a sodium halide salt or a calcium halide salt or the like. The amount and concentration of aqueous alkali metal hydroxide is suitably any which results in formation of epoxide. The amount of the inorganic base used is not particularly limited. In some embodiments, the amount of the inorganic base used may range from 1.0 to 1.5 times stoichiometric based on moles of halohydrin and any neutralizable halogenating agent that may be present, such as HCl. In other embodiments, the amount of inorganic base used may range from 1.01 to 1.3 times stoichiometric; and from 1.02 to 1.1 times stoichiometric in other embodiments. High concentration of aqueous alkali metal hydroxide may reduce the water loading into the system and the wastewater produced. A concentration of at least about 1% by weight aqueous alkali metal hydroxide or its halide salt may be used in some embodiments; at least about 5% by weight in other embodiments; at least about 10% by weight in other embodiments; at a concentration within the range from about 10 to about 50% by weight in other embodiments; and at a concentration within the range from about 5 to about 35% by weight in yet other embodiments. The concentration used should be such that during and after the reaction, the alkali metal chloride does not precipitate from solution.

Conditions of temperature and pressure are not critical in the mixer/reactor, and any under which the halohydrin and aqueous alkali metal hydroxide react to produce at least one epoxide are suitable. The rate of halohydrin reaction with the base, such as, for example, propylene chlorohydrin, with caustic in an amount of 8 wt. % sodium hydroxide, is very fast, requiring about 1 second to result in 99.5 mole percent conversion at a temperature of 90° C. The temperature and pressure may be controlled to prevent halohydrin vaporization. For example, for propylene chlorohydrin, this would be less than about 95° C. at one atmosphere pressure (101.3 kPa). The combined feed temperature, in some embodiments, is at least about 40° C.; in the range from about 40° C. to about 80° C. in other embodiments; and in the range from about 55° C. to about 80° C. in other embodiments. Residence time of the reactants in the mixer/reactor may be greater than 10 ms and up to 60 s in some embodiments; up to 15 seconds in some embodiments; up to 10 seconds in other embodiments; from about 0.01 to about 15 seconds in other embodiments; and from about 1 to about 10 seconds in yet other embodiments.

After at least a portion of the halohydrin has been converted to epoxide in the mixer/reactor, the reaction mixture may be fed to a reactive distillation column for completion of the reaction and recovery of the epoxide. This may be achieved by any process which results in separation of the epoxide. Such processes may include distillation and steam stripping, for example, such as disclosed in JP06025196B and U.S. Pat. Nos. 4,634,784 and 5,532,389. As an example of epoxide recovery, the effluent from the reactor/mixer, containing epoxide, may be fed to an azeotropic distillation column. The water and epoxide may be recovered as an overheads fraction, which may be condensed to form two phases. The aqueous phase may be refluxed back to the column, and the crude organic phase may be forwarded to purify and recover the epoxide.

Production of epoxides in a mixer/reactor according to embodiments disclosed herein may be exemplified by the production of epichlorohydrin from a mixture of 1,3-dichlorohydrin and 2,3-dichlorohydrin, as describe in WO 2006/020234. Benefits of the mass transfer attained by mixer/reactors disclosed herein, including high selectivity, high conversion, and low hydrolysis rates, may be exemplified where a ratio of the 1,3-dichlorohydrin isomer to the 2,3-dichlorohydrinl isomer is greater than 10 to 1, and the base is sodium hydroxide.

As most of the incoming dichlorohydrin is the faster reacting 1,3-isomer, most of the reaction will take place in the mixer/reactor step. The dehydrochlorination rate of the 1,3-dichlorohydrin is much faster than the epichlorohydrin hydrolysis rate in the presence of a base. However, in a biphasic system, the reaction rate is determined by the mass transfer of the dichlorohydrin from the organic phase to the aqueous alkali reaction medium. A mass transfer rate allowing for epichlorohydrin to remain in the aqueous phase for an extended period would allow more time for the epichlorohydrin produced to hydrolyze. A mixer/reactor, according to embodiments disclosed herein, providing a shear level to disperse the organic phases to a mean droplet size of about 200 microns or less, improves mass transfer, and may result in a high halohydrin conversion and selectivity, where each may be in excess of 97 percent.

All reactions take place primarily in the aqueous phase with the base. As the 1,3-dichlorohydrin and HCl are both very fast reactions and are mass transfer limited, each as described above, a high degree of segmentation is required in the reaction zone to achieve good epichlorohydrin yield. By providing efficient mixing, the HCl can be neutralized rapidly and most of the caustic can be reacted (out-competed) by the 1,3-dichlorohydrin to minimize the acid and base concentrations in the aqueous reaction phase. Mass transfer provided by mixer/reactors according to embodiments disclosed herein may limit the time for the hydrolysis reaction to occur. With the mass transfer rates achieved with mixer/reactors according to embodiments disclosed herein, feed temperature and residence time have less of an impact on epichlorohydrin yield.

Dehydrohalogenation according to embodiments disclosed herein may result in a high selectivity to the epoxide, even at high halohydrin conversions. For example, in some embodiments, the dehydrohalogenation may result in a halohydrin conversion of at least 97 mole percent and a selectivity to the epoxide of at least 97 percent; a selectivity of at least 98 percent in other embodiments. In other embodiments, the dehydrohalogenation may result in a halohydrin conversion of at least 98 mole percent and a selectivity to the epoxide of at least 98 percent; and a conversion of at least 99 mole percent at a selectivity of at least 98 percent in yet other embodiments.

EXAMPLES

A dichloropropanol feed (72% 1,3-dichloropropanol, 3% 2,3-dichloropropanol, 5% hydrochloric acid, and 20% water, by weight is reacted with a 20% sodium hydroxide aqueous solution using different mixer configurations, as given in Table 1. The pipe mixer/reactor is 1.27 cm (0.5 inches) in diameter and provides 4 seconds residence time at the flow rates used. The mixing elements used are impingement shear mixers (high and low) and helical style static mixers along the pipe. The impingement mixer is designed so that the two streams entering the mixing zone have approximately equal jet momentum defined as mass flow rate multiplied by the average velocity in the entrance channel. The jets are aligned directly opposed (180 degree angle) so as to cause direct impingement. In the present example, a "high shear" mixer consists of a 1 mm entrance hole diameter for organic flow and 3 mm entrance hole diameter for aqueous flow. A "low shear" mixer consists of a 3 mm entrance hole diameter for organic flow and 9 mm entrance hole diameter for aqueous flow. The chamber diameter is 9 mm. After a distance of about 1.7 chamber diameters, the exit flow from the impingement mixer enters, optionally as indicated in Table 1, a helical static mixer of either 0.5 m or 1.0 m in length. The length-to-diameter ratio of a helical mixer element is 1.5.

Both feed streams are heated to get the appropriate mixture temperature, then the feeds are passed through the mixer at sufficient velocity to obtain the biphasic mixture. The effluent from the pipe mixer/reactor is fed to a distillation column operating at an overhead pressure of 300 millibar. The column is operated at a reflux to feed mass ratio of 1.5. The distillate is condensed at 40° C. and phase separated. The aqueous phase is refluxed back to the column. The organic phase is analyzed to determine the conversion and yield. Results of the experiments are presented in Table 1.

TABLE 1

| Exp. # | Maximum Power per Mass (W/kg) | Yield Loss (%) |
| --- | --- | --- |
| 1 | 324 | 1.3 |
| 2 | 511 | 1.3 |
| 3 | 8.7 | 1.3 |
| 4 | 7.1 | 1.4 |
| 5 | 4.4 | 1.2 |
| 6 | 0.2 | 2.3 |

Table 1 shows that good yields and conversions are attained when the power per mass is at least 0.2 W/kg in a mixing section in the feed pipe (Exp. 6). Better yields result when the power per mass is at least 3 W/kg (Exp. 1-5). The residence time in the defined mixing zone of the impingement mixer is 45 to 61 milliseconds in these experiments, and for the static mixer the residence time is 1.4-3.3 seconds.

As described above, embodiments disclosed herein may provide for reaction of halohydrins with a base to form epoxides at a high selectivity and a high yield. For example, embodiments disclosed herein may advantageously provide for maintaining conversion by reducing epichlorohydrin hydrolysis in the mixer/reactor system of a low water dehydrochlorination process to produce epichlorohydrin. The method maintains a simple pipe with internal mixing elements to generate a minimum shear level to disperse the biphasic system in the mixer/reactor to provide efficient mass transfer. This translates to improved reaction rates of 1,3-dichlorohydrin and HCl, decreasing the acid and base concentrations in the aqueous phase as rapidly as possible to lessen the impact of hydrolysis. With the improved mass transfer rates, feed temperature and residence time have a decreased impact on epichlorohydrin yield. Another advantage of the reaction system disclosed herein is that it allows high epichlorohydrin yields with the benefits of less wastewater and better steam and alkali usage.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for producing epoxide, the process comprising:
   (a) mixing (a1) an organic phase comprising at least one halohydrin with (a2) at least one aqueous phase comprising at least one base; wherein the mixing is carried out in a plug-flow mixer/reactor system sufficient to disperse the organic phase in the aqueous phase such that the combined organic phase and aqueous phase form a mixture comprising at least two liquid phases; and imparts a power-to-mass ratio of at least 0.2 W/kg; and
   (b) converting at least a portion of the at least one halohydrin to an epoxide.

2. The process of claim 1, wherein the organic phase further comprises at least one haloacid.

3. The process of claim 1, comprising further the steps of:
   (c) feeding at least a portion of the mixture from the mixer/reactor system to a reactive distillation column;
   (d) concurrently in the reactive distillation column of step (c):
      (i) reacting at least a portion of the at least one halohydrin present in the mixture with the at least one base present in the mixture to form additional epoxide in the reactive distillation column; and
      (ii) stripping water and halohydrin from a basic aqueous residue;
   (e) recovering water and epoxide from the reactive distillation column as an overheads fraction; and
   (f) condensing and phase separating the overheads fraction of step (e) to form (i) an organic overheads fraction comprising an epoxide and (ii) an aqueous overheads fraction comprising water.

4. The process of claim 3, comprising further the step of:
   (g) returning at least a portion of the aqueous overheads fraction to the reactive distillation column as reflux.

5. The process of claim 1, wherein a concentration of the at least one base or its halide salt in the aqueous phase mixed in the plug-flow mixer/reactor system is within the range from about 5 weight percent to about 35 weight percent;
   wherein the mixing is carried out at a temperature within the range from about 40° C. to about 80° C.;
   wherein a conversion of the halohydrin is at least 98 mole percent, and
   wherein a selectivity to the epoxide is at least 98 mole percent.

6. The process of claim 1; wherein the at least one halohydrin consists essentially of dichlorohydrin and the epoxide consists essentially of epichlorohydrin.

7. The process of claim 1 or claim 6, wherein the plug-flow/mixer reactor system comprises a mixing device imparting a power-to-mass ratio of at least 3 W/kg.

8. The process of claim 6, wherein the organic phase comprises:
   55 to less than 100 percent 1,3-dichloro-2-propanol;
   up to 10 weight percent 2,3-dichloro-1-propanol;
   up to 10 weight percent HCl; and
   up to 25 weight percent water.

9. The process of claim 6, wherein the organic phase further comprises hydrogen chloride.

10. The process of claim 1 or claim 6, wherein the mixing of the organic phase and the basic aqueous phase in the plug-flow/mixer reactor system comprises a mixing time in the range from about 10 milliseconds to less than about 60 seconds.

11. The process of claim 3, wherein the halohydrin consists essentially of dichlorohydrin and the epoxide consists essentially of epichlorohydrin.

12. The process of claim 11, comprising further the step of:
   (g) returning at least a portion of the aqueous overheads fraction to the reactive distillation column as reflux.

13. The process of claim 1 or claim 6, wherein the at least one base comprises at least one of sodium hydroxide and calcium hydroxide.

14. The process of claim 13, wherein the aqueous phase mixed in the plug-flow/mixer reactor system further comprises at least one of a sodium halide salt and a calcium halide salt.

15. The process of claim 6:
   wherein a concentration of the at least one base or its halide salt in the aqueous phase mixed in the plug-flow/mixer reactor system is within the range from about 5 weight percent to about 35 weight percent;
   wherein the mixing is carried out at a temperature within the range from about 40° C. to about 80° C.;
   wherein a conversion of the chlorohydrin is at least 98 mole percent; and
   wherein a selectivity to the epichlorohydrin is at least 98 mole percent.

* * * * *